United States Patent [19]

Matsushita et al.

[11] Patent Number: 5,420,041
[45] Date of Patent: May 30, 1995

[54] METHOD OF ACID VALUE DETERMINATION BY INFRARED ABSORPTION

[75] Inventors: Kazuhiko Matsushita; Hiroshi Yokota; Keiji Fujita; Akihiro Tsukamoto, all of Kyoto, Japan

[73] Assignee: Kurashiki Boseki Kabushiki Kaisha, Okayama, Japan

[21] Appl. No.: 125,151

[22] Filed: Sep. 23, 1993

[30] Foreign Application Priority Data

Sep. 28, 1992 [JP] Japan .................................. 4-257963
Sep. 7, 1993 [JP] Japan .................................. 5-221818

[51] Int. Cl.$^6$ ...................... G01N 33/03; G01N 33/26
[52] U.S. Cl. .................................... 436/61; 73/61.48; 250/339.11; 250/341.8; 436/60; 436/129; 436/171
[58] Field of Search ...................... 436/60-61, 436/129, 171; 250/341, 339, 343, 301; 73/53.01, 61.48

[56] References Cited

U.S. PATENT DOCUMENTS 5,049,742  9/1991  Hosonuma et al. ................. 250/301

OTHER PUBLICATIONS

Handbook of Spectroscopy, vol. II, J. W. Robinson, Editor, CRC Press, Boca Raton Fla. (1974) p. 69.
Seifert et al. "Interfacially Active Acids in a California Crude Oil", Anal. Chem, vol. 41 No. 4 (1969) pp. 554–562.
Patent Abstracts of Japan vol. 15 No. 92 "Auto-Esterification Process" 02-306936 (1991).
Patent Abstracts of Japan vol. 5 No. 96 "Method for Detecting Reaction Progress by Using Infrared Ray Spectroscope" 56-39446 (1981).

*Primary Examiner*—James C. Housel
*Assistant Examiner*—Jan M. Ludlow
*Attorney, Agent, or Firm*—Foley & Lardner

[57] ABSTRACT

A method of determining acid value with high accuracy, using an infrared spectrometer is provided, in which the absorbance is determined attributable to carboxylic group based on an infrared absorption spectrum at wave numbers around 3300 cm$^{-1}$.

4 Claims, 3 Drawing Sheets

METHOD OF ACID VALUE DETERMINATION BY INFRARED ABSORPTION

FIELD OF THE INVENTION

The present invention relates to a method of acid value determination based on utilization of infrared absorption.

PRIOR ART

At present, quality analysis of material oil in fats and oils manufacturing process and quality analyses in refining process and decoloration and deodorization processes are manually performed by titration. Among other items of quality analyses, acid value is a particularly important item which sways product's quality, for which a highly responsible feedback control not susceptible to personal difference among individuals who perform the analysis, variation nor one-sidedness of measurement results is desired. Against this background, in recent years, attempt is being made to use optical analysis in making continuous monitor of acid value etc. in reaction solutions for detection of the state of processes of manufacturing fats and oils and resins, etc.

It is generally well-known that an infrared characteristic absorption band of organic acids i.e.—COOH group exists at wave numbers around 1710 $cm^{-1}$. Absorptivity of —COOH group in this absorption band is very large. Therefore, for measurement of its absorbance, thickness of sample layer must be much reduced, so it is necessary to prepare a thin film or a cell with a length of about several $\mu m$—several tens $\mu m$ using the liquid filming method or the like.

As another method of acid value determination, utilizing the absorption depending on —COOH group in other wave number ranges, a method of determining whereabouts of —COOH group in a reaction solution from absorbance at a 2530 $cm^{-1}$ wave number, using an infrared spectrometer is disclosed (Japanese Patent Application No. Sho 54-115605). At this wave number, the absorptivity of —COOH group is very small.

Methods of measuring acid value of carboxylic acids, hydroxide value of alcohols and ester value of esters from absorption of near infrared rays are also disclosed (Japanese Patent Application No. Hei 1-128454).

In measuring absorbance at wave numbers around 1710 $cm^{-1}$ depending on —COOH group, a very thin sample layer i.e. a thin cell should be used, as hereinabove described, and its handling needs technique and experience. When a high viscosity measurement sample is filled into the cell, the cell is liable to break-down because of the high pressure applied onto the cell opening. Particularly, when the measurement is made, using a flow cell type cell, while circulating the sample, this problem is prominent.

In measuring absorption around the wave number of 1710 $cm^{-1}$, the conventional infrared spectrometer has substantially lower performance at wave numbers below 2000 $cm^{-1}$, as compared with a wave number range of 4000-2000 $cm^{-1}$. In a wave number range below 2000 $cm^{-1}$, generally, TGS is used as a detector, which is inferior by more than one order in sensitivity, as compared with PbS or PbSe which is typically used in a region of 4000-2000 $cm^{-1}$. Selection of optical material is difficult. Because such deliquescent materials as KBr, NaCl, etc., are used as window materials, nitrogen purge is necessary. In a range below a wave number of 1800 $cm^{-1}$, high precision interference filters are not available. There are such other problems.

Absorptivities at wave numbers around 2530 $cm^{-1}$ depending on —COOH group are extremely small. It is therefore possible to utilize relatively thick cells. There exist, however, a very large absorption of CH groups in its proximate region, so that the absorption peak due to —COOH group tends to be masked by the CH group's peak. For this reason, high precision measurement can hardly be made even using a high precision infrared spectrometer.

In the near infrared region, not only no normal frequency absorption based on —COOH group takes place, but absorption peaks overlap and absorptivities of measurement objects are very small; measurement for high precision determination is therefore impossible. The measured value varies with varying iodine values. For the reasons hereinabove mentioned, complex data processing needs to be performed, to determine the acid value at near infrared region, and only a small change in the measurement conditions for this complex data processing may lead to extreme vicissitude of measured values, which is really a grave concern.

SUMMARY OF THE INVENTION

The present invention has as its object providing a method of acid value determination which permits the measurement to be made with high accuracy using a conventional instrument and a cell, when measuring acid value by use of an infrared spectrometer.

Thus the present invention relates to a method of acid value determination comprising determining the acid value attributed to a carboxylic group based on an infrared absorption spectrum at wave numbers around 3300 $cm^{-1}$.

When acid value was determined by the method of the present invention, standard deviation of analytical curve was cut down to about 1/10 of that which occurs when the determination is made from absorptions at wave numbers around 2530 $cm^{-1}$ and the value of coefficient of correlation rose, thus registering a leaps and bounds improvement in accuracy. Further, it permits the measurement to be taken using a relatively thick cell, thus making it possible to make automatic measurement of acid value by the method of this invention in manufacturing process of fats and oils, etc. By the method of this invention, acid value of not only fatty acids but such mineral oils as engine oil and the like can be measured with high accuracy. For example, it may be used to provide an index of deterioration of engine oil.

BRIEF DESCRIPTION OF THE DRAWINGS

These and other objects and features of the present invention will become clear from the following description taken in conjunction with the preferred embodiments thereof with reference to the accompanying drawings throughout which like parts are designated by like reference numerals, and in which.

DETAILED DESCRIPTION OF THE PREFERRED EMBODIMENTS

Figure 1:
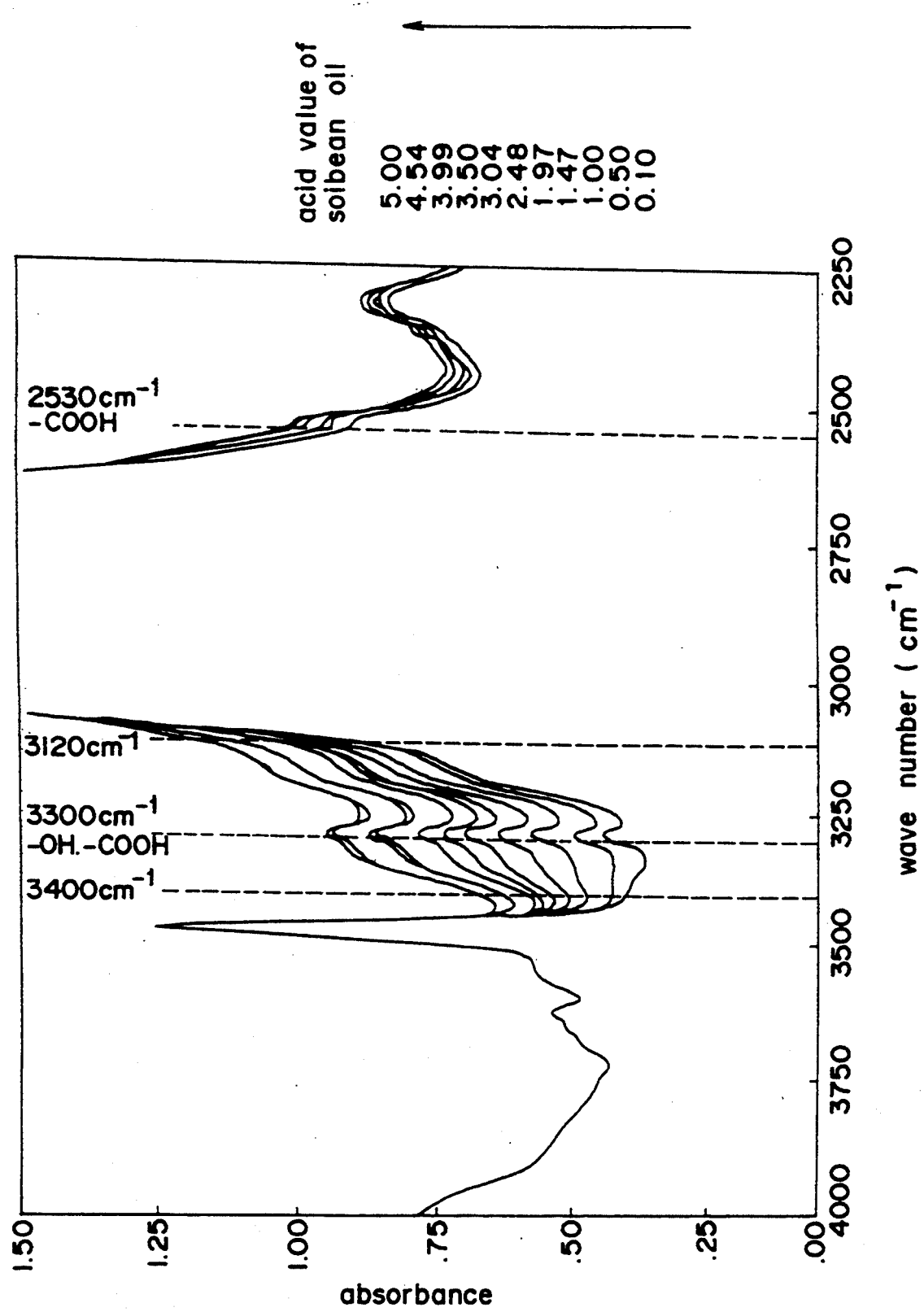
FIG. 1 shows a chart of infrared absorption spectra for measurement with 11 samples of soybean oil.

Generally, characteristic absorption bands depending on —COOH group are known to exist at wave numbers around 1710 cm$^{-1}$ and 2530 cm$^{-1}$. Besides, there exists an absorption band at wave numbers around 3300 cm$^{-1}$ which is known to be attributable to —OH group, but it has not been known at all that it coincides with that of —COOH group. This absorption band, overlapped as that of —OH, is generally regarded as inadequate for the determination of —COOH group. However, with materials not containing substantial amount of water or —OH group, like fats and oils, the determination of —COOH group may be made with high accuracy from an infrared absorption spectrum at wave numbers around 3300 cm$^{-1}$.

Even for a system containing a relatively large number of —OH groups, —COOH groups therein may be determined using appropriate correcting means. In particular, in one method, the absorbance of —OH group is measured separately by the conventional method and this absorbance of —OH group is subtracted from the total of —COOH and —OH groups as measured based on the infrared absorption at wave numbers around 3300 cm$^{-1}$. Further, both of the —COOH group and the —OH group can be easily and simultaneously determined from the infrared absorption spectrum by correcting the —COOH group content obtained from the IR absorbance around 3300 cm$^{-1}$ based on the —COOH group content obtained from a conventional method using IR absorbance around 2530 cm$^{-1}$.

Furthermore, an ester group can be also obtained by the determination of the IR absorbances of around 3300 cm$^{-1}$ and of around 3470 cm$^{-1}$ of a —CO group, which enable to give a knowledge of an ester value.

Further, to exclude a region of 3410 cm$^{-1}$-3300 cm$^{-1}$ where the measurement is liable to be influenced by the water content in fats and oils, the wave number is limited to 3300 cm$^{-1}$-3050 cm$^{-1}$. In that way, data very little influenced by water content are obtained. If this region is employed, even if water contents in fats and oils vary due to difference in manufacture lot or ambient conditions such as humidity etc., highly accurate data can be obtained.

The absorbance around the wave number of 3300 cm$^{-1}$ attributed to a —COOH group is 0.1 per an acid value of 1 and a cell length of 1 mm, which is extremely lower in the sensitivity than that around 1710 cm$^{-1}$ is, i.e. 1.8. For this reason, as differentiated from the measurement of absorbance at wave numbers around 1710 cm$^{-1}$, this measurement may be made using samples of relatively thick layers. Thus the usual problem is solved.

As the sample cell used in the determination method of this invention, whatever is normally used to hold the sample to be measured in an IR spectrometer is usable, for example, a quartz, a fluorite, a sapphire and the like, which may be square cells, flow cells or the like may be preferably employed to measure the acid value of fats and oils. The cell should preferably have such a thickness that it accommodate a sample layer with a thickness of 0.1–10 mm, particularly 0.5–5 mm. Thick sample layer keeps variation in measurement small, permitting the measured value to be obtained with high accuracy. Further, even if the sample has high viscosity, like fats or oils, etc., its filling and cleaning is relatively simple and its replacement in the cell is easy.

It is also possible to install a flow cell in an infrared spectrometer and allow the sample to continuously pass therethrough, thereby continuously monitoring the acid value during the reaction process of fats and oiles or the like. Because of the large thickness of the cell, the sample to be analyzed may be continuously circulated, without being held up in the cell, even when the flow cell is used. Moreover, cells capable of withstanding high temperature and high pressure conditions which are often required in continuous analysis may be relatively readily obtained. As the flow cells, all conventionally available ones may be favorably put to use. For example, the one disclosed by Japanese Patent Application No. Sho 54-115605 is recommended. Further, with highly scattering samples, the measurement may be made by transmittal reflection measuring method or diffuse reflection measuring method, using a cell configuration which is adapted to capture not only transmitted light but diffuse-reflected light.

In the method of acid value determination of the present invention, acid value is calculated from absorbance at wave numbers around 3300 cm$^{-1}$ which are attributable to —COOH group. In determining absorbance, normally the measurement of absorbance is made beforehand with air as a reference sample and it is calculated by Formula I from this reference and the measured value with the object sample to be measured:

$$\text{Absorbance} = -\log_{10} \frac{\text{Measured value with object sample to be measured}}{\text{Measured value with reference sample}} \quad \text{I}$$

However, preferably, the determination accuracy is improved by using a reference sample (a fatty acid or designated oil or fat, etc.) which is akin to the oil or fat of the object to be measured.

Such materials usable as the reference sample include fats and oils, caproic acid, lauric acid, myristic acid, palmitic acid, stearic acid and other saturated fatty acids, palmitoleic acid, oleic acid, linolic acid, linolenic acid, eicosanic acid and other unsaturated fatty acids, and acetone, hexane, ethanol, triacetylene, glycerine, ethyl acetate, butyl acetate, amyl acetate, tripalmitin, trimyristin, liquid paraffin, etc. The reference sample must be liquid in the measurement temperature range.

In the method of acid value determination of the present invention, absorption is measured of a plurality of object samples to be measured whose acid values are known and a reference sample at wave numbers around 3300 cm$^{-1}$ and from the data thus obtained, absorbance is calculated for each sample, to establish a calibration curve which represents the correlation between absorbance and acid value. A Formula II is obtained from calibration curve:

$$C = P_1 A + P_0 \quad \text{II}$$

where A denotes absorbance, $P_1$ and $P_0$ coefficients, and C acid value. The coefficients $P_1$ and $P_0$ are values determined by the least squares method, to minimize the difference between true acid value and the one calculated from the Formula II. Using this Formula II, acid value of any unknown sample is determined from the absorbance at wave numbers around 3300 cm$^{-1}$. As a formula, an nth order formula as shown in Formula III is sometimes used:

$$C = \sum_{i=1}^{n} P_i A^i + P_0 \quad \text{III}$$

Further, as an additional means, to eliminate any influence of equipment fluctuation error of the infrared spectrometer, the absorbance of the absorption-free region (e.g. around a 4000 cm$^{-1}$ wave number for measurement of fats and oils) is determined, and then a value A' resulting from subtracting the determined value from each absorbance:

A'=(absorbance around a 3300 cm$^{-1}$ wave number) −(absorbance around a 4000 cm$^{-1}$ wave number)

may be used instead of the absorbance A for each sample.

According to this invention, samples having acid values from 0 to approx. 200 may be measured. As alternatives, for elimination of turbidity of sample and scattering and instrument variation, primary or secondary differentiation of the absorbance at wave numbers around 3300 cm$^{-1}$ may be used.

The present invention provides a device for determining an acid value of a sample not containing a substantial amount of water and —OH group. The device according to the present invention is furnished with an infrared spectrometer capable of determining an absorbance of infrared spectrum at the wave number of at least from 3410 cm$^{-1}$ to 3050 cm$^{-1}$, especially 3300 cm$^{-1}$ to 3050 cm$^{-1}$.

The infrared spectrometer of device of the invention may be capable of determining the absorbance of another spectrum such as at a wave number around 4000 cm$^{-1}$ in case of oil and fat in order to eliminate any influence of equipment fluctuation error of an infrared spectrometer, or at another wave number around such as 1710 cm$^{-1}$ or 2530 cm$^{-1}$ for reference.

The sampling cell used in the device of the present invention may have a layer thickness of a sample layer, such as 0.1–10 mm, more preferably 0.5–5 mm according to the aforementioned ground.

The device of the present invention is also furnished with a calculating system which can calculate a content of a —COOH group in a sample from an absorbance attributed to the —COOH group within a range of the wave number of from 3410 cm$^{-1}$ to 3050 cm$^{-1}$, preferably from 3300 cm$^{-1}$ to 3050 cm$^{-1}$.

The calculating system used in the present device may be a computer which is previously programmed according to the aforementioned formulae as referring to another absorbance or as using primary or secondary differentiation of the absorbance as aforementioned.

EXAMPLES

The present invention is now described in more detail with reference to examples and comparative examples thereof.

With commercially available soybean oil to which was added various amounts of a fatty acid of known acid values as samples, absorbance at wave numbers of 4000-2250 cm$^{-1}$ was measured by an infrared spectrometer. Then from absorbances at wave numbers of 3300 cm$^{-1}$, 3400 cm$^{-1}$ and 3120 cm$^{-1}$ (Examples) and absorbance at 2530 cm$^{-1}$ (Comparative Example), calibration curves were obtained. Then using them, respective acid values were determined.

Measurement conditions
  Instrument used: Nicolet FTIR740
  Samples to be measured: Eleven types of fats and oils samples prepared by adding varying amounts of a fatty acid to a commercially available soybean oil so that its acid value to be 0.1–5.0.
  Reference sample: Air
  Cell for measurement: 1 mm Quartz cell
  Measurement wave number region: 4000-2250 cm$^{-1}$
  Temperature at the time of measurement: 25° C.

Infrared absorption spectra measured with these 11 samples under the above-mentioned conditions are shown in FIG. 1.

Calculation of acid value

EXAMPLE 1

Figure 2:
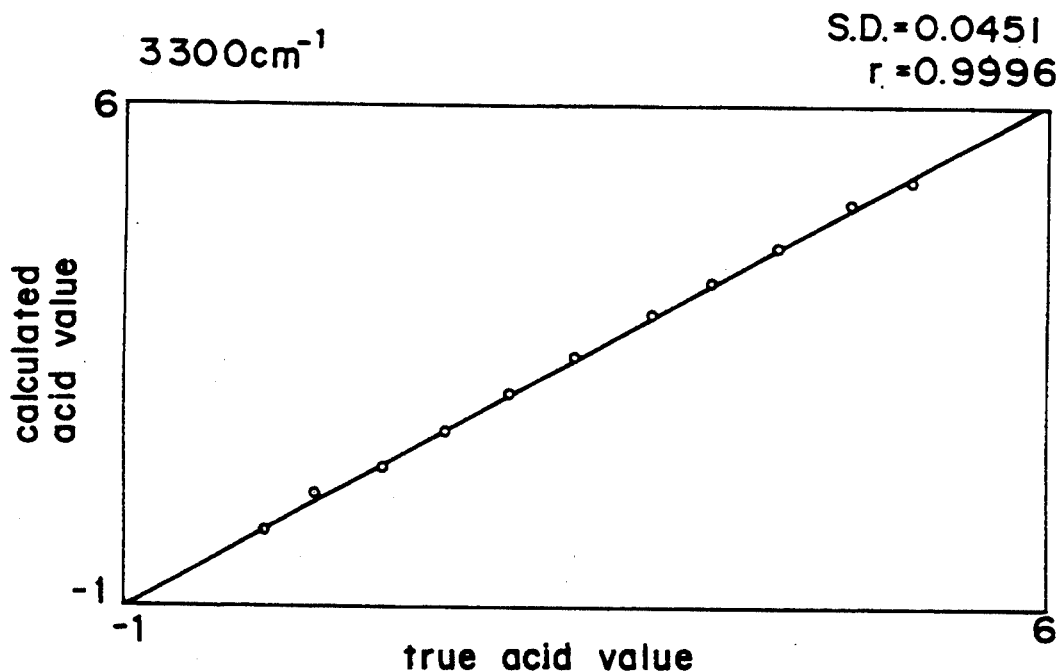
FIG. 2 depicts a correlation diagram between the acid value obtained by the determination method of this invention and true acid value.

Signal strength was read at a measurement wave number of 3300 cm$^{-1}$ and a wave number of 3800 cm$^{-1}$ in a region where no absorption occurs and from the results, absorbance of each sample was calculated by Formula I. From this absorbance and true acid value, Formula II was obtained by way of the least squares method. The true acid value was determined by the titration method specified by the Fats and Oils Inspection Association. A correlation diagram plotting against the true value the acid value, as calculated from Formula II, is depicted in FIG. 2. Standard deviation (S.D.) was found to be 0.0451 and, coefficient of correlation (r) 0.9996.

EXAMPLE 2

With wave numbers of 3400 cm$^{-1}$ and 3120 cm$^{-1}$ employed as the measurement wave numbers, signal strength was read at each wave number and at a wave number of 3800 cm$^{-1}$ being in a region was no absorption occurs and then Formula II were obtained from each related data in the same way as in Example 1. Coefficients of correlation between true acid value and the calculated value thus obtained were 0.9993 and 0.9998, respectively.

COMPARATIVE EXAMPLE

Figure 3:
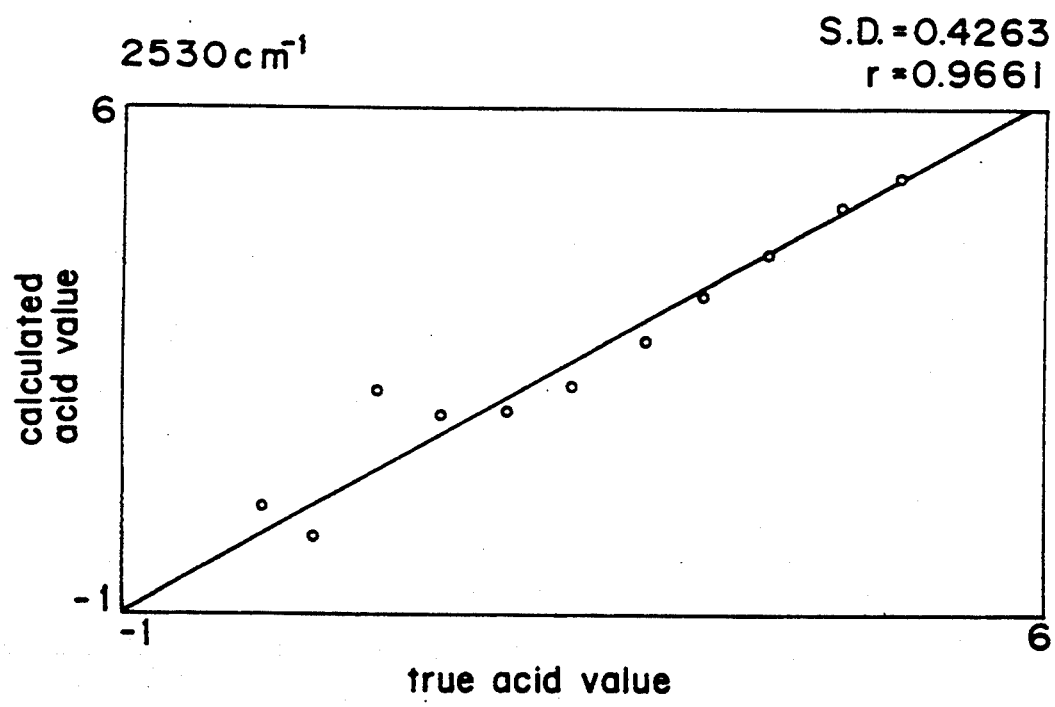
FIG. 3 depicts a correlation diagram between the acid value obtained by the prior art method and true acid value.

Signal strength was read at a measurement wave number of 2530 cm$^{-1}$ and at a wave number of 3800 cm$^{-1}$ where no absorption occurs and from these data, a Formula II was obtained in the same way as in Example 1. A correlation diagram between true acid value and the calculated value is put up in FIG. 3. Standard deviation was found to be 0.4263 and coefficient of correlation 0.9661.

EXAMPLE 3

Changes in acid value of commercially available engine oil due to its deterioration were measured.

Measurement conditions
  Instrument used: Nicolet FTIR740
  Sample to be measured: Engine oil (SF 10W −40; mfd. by Autobuccs K. K.), used in a car (Cresta; TOYOTA K. K.) of which three samples: unused, after running. 4000 km, and after running 7000 km. True values of acid value of respective samples determined by a titration method were 1.29, 1.8, and 2.18, respectively.
  Reference sample: Air
  Cell for measurement: 1 mm Quartz cell
  Measurement wave number region: 4000-2750 cm$^{-1}$
  Temperature at the time of measurement: 25° C.

Figure 4:
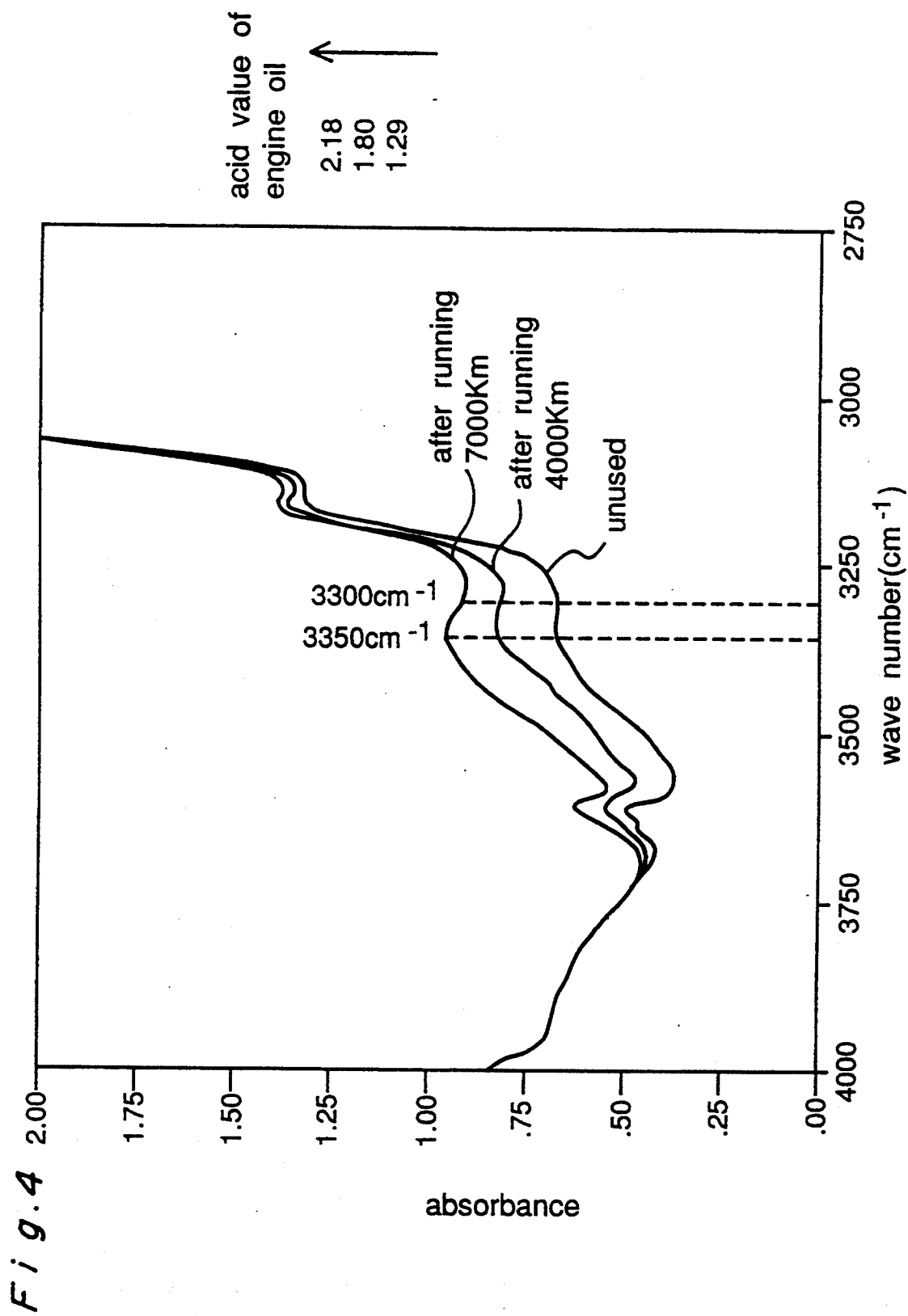
FIG. 4 shows a chart of infrared absorption spectra for measurement with engine oil.

Infrared absorption spectra of three samples measured under the above-mentioned conditions are depicted in FIG. 4.

Calculation of acid value

Signal strength was read at a measurement wave number of 3350 cm$^{-1}$ and at a wave number of 3950 cm$^{-1}$ in a region where no absorption occurs and from these data, absorbance of each sample was calculated. From this absorbance and the true acid value measured for each sample, an analytical curve formula based on Formula II was calculated by way of the least squares method. The true acid value was determined in compliance with the titration method according to JIS K 2501. Coefficient of correlation between true acid value and calculated value was found to be 0.9997.

What is claimed is:

1. A method of determining an acid value of a sample of fats and oils which comprises measuring the infrared absorption spectrum of the sample at wave numbers around 3300 cm$^{-1}$, wherein the sample has a thickness of 0.1–10 mm, and determining the acid value of the sample based on the absorption spectrum.

2. A method according to claim 1, wherein the thickness of the sample is 0.5–5 mm.

3. A method of determining the acid value of a sample of fats and oils which comprises measuring the infrared absorption spectrum of the sample at wave numbers of 3410-3050 cm$^{-1}$, wherein the sample has a thickness of 0.1–10 mm, and determining the acid value of the sample based on the absorption spectrum.

4. A method of determining the acid value of a sample of fats and oils which comprises measuring the infrared absorption spectrum of the sample at wave numbers of 3300-3050 cm$^{-1}$, wherein the sample has a thickness of 0.1–10 mm, and determining the acid value of the sample based on the absorption spectrum.

* * * * *